United States Patent [19]

Gray

[11] Patent Number: 5,014,361

[45] Date of Patent: May 14, 1991

[54] POLYURETHANE ELASTIC GLOVE HAVING IMPROVED PUNCTURE AND TEAR RESISTANCE

[75] Inventor: Norman Gray, Cary, N.C.

[73] Assignee: Aukland (USA), Inc., Cary, N.C.

[21] Appl. No.: 480,610

[22] Filed: Feb. 15, 1990

Related U.S. Application Data

[62] Division of Ser. No. 257,450, Oct. 13, 1988, Pat. No. 4,917,850.

[51] Int. Cl.⁵ ............................................. A41D 19/00
[52] U.S. Cl. ............................................ 2/167; 2/168
[58] Field of Search ............... 2/161 R, 167, 168, 169, 2/159

[56] References Cited

U.S. PATENT DOCUMENTS

| | | | |
|---|---|---|---|
| 2,335,871 | 12/1943 | Milligan | 2/168 |
| 3,094,704 | 6/1963 | Abildgaard | 2/167 |
| 3,148,235 | 9/1964 | Velonis et al. | 264/301 |
| 3,197,786 | 8/1965 | Velonis et al. | 2/167 |
| 3,798,200 | 3/1974 | Kaneko et al. | 528/76 X |
| 3,879,764 | 4/1975 | Weber-Liel | 2/167 |
| 3,963,681 | 6/1976 | Kaneko et al. | 528/76 X |
| 4,000,117 | 12/1976 | Shah | 260/48 |
| 4,131,604 | 12/1978 | Szycher | 528/76 X |
| 4,463,156 | 7/1984 | McGary, Jr. et al. | 528/65 |
| 4,519,098 | 5/1985 | Dunmire et al. | 2/168 |
| 4,523,005 | 6/1985 | Szycher | 528/76 |
| 4,660,228 | 4/1987 | Ogawa et al. | 2/167 |
| 4,670,330 | 6/1987 | Ishiwata | 2/167 X |
| 4,684,490 | 8/1987 | Taller et al. | 264/296 |
| 4,783,857 | 11/1988 | Suzuki et al. | 2/167 |

*Primary Examiner*—Werner H. Schroeder
*Assistant Examiner*—Sara M. Current
*Attorney, Agent, or Firm*—Waldron & Associates

[57] ABSTRACT

A polyurethane glove having improved tear and puncture resistance is made from the reaction product of an aliphatic diisocyanate, an aliphatic polyether diol having a molecular weight in the range of about 1,000 to about 5,000 and an aliphatic diol containing about 2 to about 6 carbon atoms.

6 Claims, No Drawings and tear resistance of such prior art gloves.
POLYURETHANE ELASTIC GLOVE HAVING IMPROVED PUNCTURE AND TEAR RESISTANCE This is a divisional of application Ser. No. 257,450, filed Oct. 13, 1988 and now U.S. Pat. No. 4,917,850.

BACKGROUND OF THE INVENTION

1. Field of the Invention

This invention relates to pliable and conformable gloves such as surgical gloves and more particularly to protective gloves used in medical related procedures and facilities made from a polyurethane elastomer.

2. The Prior Art

Surgical gloves are made of very thin elastomeric materials such as vulcanized natural rubber and the like and are sized to provide a tight fit forming a skin-like sheath on the hand of the wearer. The objectives of surgical glove manufacturers are to provide a glove which will impart maximum tactile sensitivity to the wearer without impairing his facility of manipulation while at the same time protecting both the wearer and the patient from cross-contamination or infection.

There are however, a number of undesirable characteristics of the prior art gloves. One such undesirable characteristic of the gloves manufactured from vulcanized natural rubber is that the gloves may cause an adverse reaction to the skin of the wearer. Approximately 5% of all surgeons and medical personnel suffer from some type of dermatitis caused by an allergy or sensitivity to the vulcanized natural rubber.

Because of their skin tight fit and nature of the vulcanized natural rubber, dry lubricants such as talc have been used to permit surgical gloves to be easily placed on the hands of the wearer. Unfortunately, talc has been known to irritate skin when brought into contact with it, thereby aggravating the dermatitis problem encountered with vulcanized natural rubber.

In addition to the skin problems encountered with surgical gloves manufactured from vulcanized natural rubber, the gloves exhibit limited physical strength and are easily torn or punctured. The increasing risk of infection encountered by health care workers in contact with contaminated body fluids from patients with infectious diseases such as AIDS makes it imperative that gloves worn by these workers have a high degree of tear and puncture resistance so as to provide maximum protection from exposure to dangerous organisms contained in these body fluids.

Another undesirable characteristic of surgical gloves manufactured of vulcanized natural rubber is the fact that they frequently contain tiny pin-holes. By virtue of the molecular make-up of vulcanized natural rubber and the dip process by which surgical gloves are normally manufactured, such tiny pin-holes do occur. Although such pin-holes are very small, they are normally large enough to allow transmission of very small blood borne viruses smaller than 10 microns, such as the AIDS and Hepatitis B viruses.

In addition to the above undesirable characteristics, hand fatigue and poor finger-tip sensation are prevalent problems due to the elastic properties of the vulcanized natural rubber.

One approach to overcome the allerginicity problem has been to manufacture surgical gloves from polyurethane compositions which are hypoallergenic. For example, McGarry, Jr. et al, U.S. Pat. No. 4,463,156 discloses the manufacture of hypo-allergenic surgical gloves from polyurethane elastomers which are the reaction products of an aromatic or alicyclic polyisocyanate and a long chain diol (500–5000 average molecular weight) that is cross-linked with a polyhydroxy cross-linking agent. Although elastic gloves manufactured from polyurethane elastomers of the type disclosed in U.S. Pat. No. 4,463,156 are hypoallergenic, a number of disadvantages are encountered with such gloves as well. For example, due to the use of a cross-linking agent in the preparation of the polyurethane elastomer, there results a glove manufacturing process that is costly, slow, and relatively complex when compared to prior glove manufacturing processes. In addition to higher glove manufacturing costs, gloves manufactured using the cross-linked polyurethane compositions when compared to vulcanized natural rubber gloves exhibit less conformity to the wearer's hand when worn. Further, the cross-linked nature of polyurethane compositions limits approval for medical grade use.

In addition to the above disadvantages of surgical gloves manufactured of cross-linked polyurethane, such gloves are rather rigid causing a high degree of hand fatigue and providing very poor finger-tip sensation.

In view of the above considerations, there is a need in the art for a surgical glove that is non-allergenic or hypoallergenic, exhibits superior tear and puncture resistance, does not tend to form pin-holes during manufacturing, minimizes hand fatigue and provides optimum finger-tip sensation.

SUMMARY OF THE INVENTION

A principal object of the present invention is to provide a hypoallergenic polyurethane elastic glove that will impart maximum tactile sensitivity to the wearer without impairing his facility of manipulation. Another object of the present invention is to provide a polyurethane glove which can be manufactured at a relatively low cost and be acceptable for medical grade applications. A further object of the present invention is to provide a polyurethane glove having a high degree of tear and puncture resistance so that the wearer and persons contacted by the wearer are provided maximum protection from contamination or infection. Still another object of this invention is to provide a surgical glove having a VICAT softening point at body temperatures to minimize elasticity and rigidity without loss of physical properties to thereby minimize the wearer's hand fatigue and enhance his or her finger-tip sensation.

These and other objects of the present invention are attained in a glove fabricated from a noncross-linked, thermoplastic polyurethane elastomeric composition which is the reaction product of an aliphatic diisocyanate, a high molecular weight polyether diol having a molecular weight in the order of about 1,000 to about 5,000 and a low molecular weight aliphatic diol containing about 2 to about 6 carbon atoms, the ratio of polyether diol to aliphatic diol being in the range of about 0.3 to about 1.7 preferably in the range of about 0.7 to about 1.3.

Polyurethane gloves made in accordance with the practice of the present invention are hypoallergenic, efficiently manufactured and exhibit extremely high puncture and tear resistance so that when compared with prior art gloves of the present invention, the gloves exhibit an improvement on the order of 3 times the puncture and tear resistance of such prior art gloves. In addition, such gloves are devoid of pin-holes and have a VICAT softening temperature below the wearer's hand temperature and thus become soft to minimize hand fatigue and enhance finger-tip sensation without the loss of physical properties.

DETAILED DESCRIPTION OF THE INVENTION AND PREFERRED EMBODIMENTS

The polyurethane compositions used to prepare gloves such as surgical gloves in accordance with the present invention are non-cross-linked thermoplastic polymers so that the gloves are rapidly made by dipping or otherwise depositing on a suitable form a solution of the polyurethane composition.

The polyurethane solution is made by dissolving solid particles of the polyurethane composition of the present invention in a suitable organic solvent such as tetrahydrofuran, dimethyl acetamide, methylene chloride or a mixture thereof at a solids concentration of about 5 to about 25% by weight of the solution and preferably about 10 to about 20% by weight of the solution. The viscosity at 55° C. is 150 to 6500 cps, and preferably 2300 cps.

After deposition of a film of the polyurethane composition of the desired thickness, it is necessary to allow the solvent to evaporate whereby a solid continuous continuous polyurethane film is formed.

In preparing the thermoplastic, solution grade polyurethane compositions useful in the practice of the present invention, stoichiometric proportions of the aliphatic diisocyanate are reacted with a mixture of the higher molecular weight polyether diol and low molecular weight aliphatic diol in the presence of a small but effective amount of a condensation catalyst such as dibutyl tin dilaurate, the ratio of polyether diol to aliphatic diol being in the range of about 0.3 to about 1.7 preferably in the range of about 0.7 to about 1.3. At such polyether diol/aliphatic diol ratios, the Shore Hardness of the polyurethane elastomer will range from 70 to 90. A Shore Hardness of 80 (Shore A) is preferred in the practice of the invention.

Aliphatic diisocyanates useful in the practice of the present invention have the formula

where R is a cycloaliphatic radical having 1 to 6 carbon atoms in a methylene bridge connecting 4-cyclohexyl isocyanates moieties and represented by the formula:

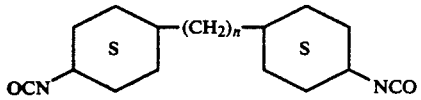

where n=1-6.

An illustrative example of such aliphatic diisocyanates is methylene bis (4-cyclohexyl) isocyanate, (HMDI), which is preferred.

Aliphatic polyether diols useful in the practice of the present invention range in average molecular weight from about 1,000 to about 5,000, the aliphatic group in the polyether diol preferably containing about 4 to about 12 carbon atoms, the aliphatic group being straight chain, or branched or cyclic. Illustrative polyether diols useful in the practice of the present invention include polytetramethyl ether glycol having a molecular weight in the range of 1,000-2,000.

A polyurethane glove prepared in accordance with the preferred form of the invention is a surgical glove formed of a polyurethane reaction product of dicyclohexyl methane diisocyanate, a polytetramethylene ether glycol having a molecular weight in the range of 1,000-3,000 and 1,4 butane diol, the molar ratio of polyether diol to butane diol being in the range of 0.7 to 1.3. Compositions of this preferred polyurethane composition are known in the art, for example Szycher, U.S. Pat. No. 4,523,005. The surgical glove generally has a thickness in the range of about 0.005 to about 0.007 inches and weighs about 7.00 grams.

The polyurethane glove of the present invention is preferably made by dipping a surgical glove form or mandrel coated with a release agent, such as a fatty acid, such as oleic acid, the mandrel being preheated to a temperature of about 60°-70° C., in a heated (50°-70° C.) bath containing a solution of the polyurethane composition to form a uniform coating on the mandrel of the polyurethane. Automatic controls, well known in the art, are useful to control the rate of immersion and withdrawal of the mandrel in the polyurethane bath. The rate of withdrawal and the number of submersions determines the glove thickness. The preferred rate of withdrawal is about 2.0 to 3.0 inches per second and thickness is about 0.007 inch. (For industrial applications, greater thicknesses are preferred up to about 0.020 inch.) After the final submersion, the mandrel is withdrawn from the bath and sufficient heat, e.g. 60°-80° C., is applied to the coated mandrel to rapidly evaporate the solvent and form a solid glove product which is thereafter removed from the mandrel. The dried coated mandrel is further coated with an antiblocking agent such as a fatty acid containing about 6 to about 30 carbon atoms, preferably oleic acid, and the glove product formed on the mandrel is thereafter removed form the mandrel. If desired, release agents such as talc and corn may be dusted on the coated mandrel, but such practices are not preferred.

The invention is further illustrated by the following example.

EXAMPLE

A polyurethane elastomer was prepared by mixing 122 grams of dicyclohexyl methane diisocyanate with a mixture of the following five constituents: 151 grams 1000 molecular weight polytetramethylene ether glycol, 24 grams of 1,4 butane diol, 3 grams of tetrakis [methylene (3,5 ditertbutyl 4-hydroxyhydrocinnamate)] methane (antioxidant), 0.5 grams of ethylene bis oleamide (extrusion lubricant) and 0.03 grams dibutyl tin dilaurate (catalyst).

The constituents were mixed and deaerated until all entrained gases were removed. The mixture was then cured at 110° C. for three hours under a nitrogen atmosphere in the form of sheets. The sheets were then converted to pellets.

A seamless surgeon's glove was formed according to the invention by dipping a group of spaced glove mandrels preheated to 65° C. into a tank containing a solution heated to 55°-60° C. containing dissolved, in methylene chloride at a concentration of 15% by weight, pellets of the polyurethane elastomer prepared in accordance with the procedure described above. The polyurethane elastomer had a Shore Hardness of 80 Shore A.

The glove forms, precoated with oleic acid, were submerged in the polyurethane elastomer bath for 3 minutes to give a coating thickness of 0.007 inch. The coating on the mandrel was dried at 70° C. in an air dryer for 15 minutes to assure that the methylene chloride was completely evaporated. The dried coating mandrel was further coated with a sterile oleic acid and the gloves were then stripped from the mandrel.

The gloves had the following physical properties:

| Property | Value |
| --- | --- |
| Percent Elongation | 770 |
| Ultimate Tensile strength (psi) | 8935 |
| Notched Resistance to Tearing (KN/m) | 305 |
| VICAT Softening Point (°F.) | 140 |
| Melt Temperature (°F.) | 280 |

For purposes of comparison, surgical gloves purchased in a surgical supply store were tested, along with the gloves produced above, for puncture resistance using ASTM D624. The results of that test were as follows:

| Source | Material | Puncture Resistance (psi) ASTM D624 |
| --- | --- | --- |
| Manufacturer A | Latex | 343 |
| Manufacturer B | Latex | 525 |
| Manufacturer C | Latex | 270 |
| Manufacturer D | Vinyl | 284 |
| Above gloves | polyurethane | 932 |

While the above description is limited to the use of the inventive material as to surgical gloves, it should be apparent that other applications of the polyurethane product could be made without departing from the spirit of the invention. For example, gloves for applications such as dental, military and laboratory use could be made of the same material and in substantially the same way. In addition, other sanitary and disease protective devices which in essence consist of thin elastic coverings, such as bandage wrapping, finger covers and prophylactics could also be made of the same beneficial polyurethane material to provide equally beneficial results without departing from the spirit of the invention.

What is claimed is:

1. A medical or surgical glove having improved tear and puncture resistance made from a formed thermoplastic polyurethane composition which is the reaction product of an aliphatic diisocyanate, an aliphatic polyether diol having a molecular weight in the range of about 1,000 to about 5,000 and an aliphatic diol containing about 2 to about 6 carbon atoms.

2. The glove of claim 1 wherein the aliphatic diisocyanate has the formula

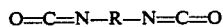

where R is a cycloaliphatic radical having 1 to 6 carbon atoms in a methylene bridge connecting 4-cyclohexyl isocyanate moieties and represented by the formula:

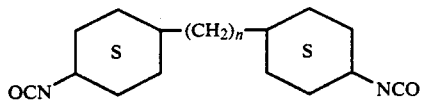

where n=1-6.

3. The glove of claim 1 wherein the aliphatic diisocyanate is methylene bis (4-cyclohexyl) isocyanate.

4. The glove of claim 1 wherein the aliphatic polyether diol has an aliphatic group containing about 4 to about 12 carbon atoms.

5. The glove of claim 1 wherein the aliphatic diol is 1,4-butane diol.

6. The glove of claim 1 wherein the polyurethane reaction product has a Shore Hardness of about 70 to about 90.

* * * * *